United States Patent [19]

Ely

[11] 4,004,345
[45] Jan. 25, 1977

[54] DISTAL RETRACTION CLAMP FOR RUBBER DAM

[76] Inventor: Sherman S. Ely, 11005 NE. 9th, Bellevue, Wash. 98004

[22] Filed: Nov. 17, 1975

[21] Appl. No.: 632,279

[52] U.S. Cl. .................................................. 32/36
[51] Int. Cl.² ........................................ A61C 5/12
[58] Field of Search ......................... 32/34, 35, 36

[56] References Cited
UNITED STATES PATENTS

| 138,370 | 4/1873 | Blake | 32/36 |
| 1,532,821 | 4/1925 | Ivory | 32/36 |

Primary Examiner—Robert Peshock
Attorney, Agent, or Firm—Seed, Berry, Vernon & Baynham

[57] ABSTRACT

A clamp for retaining a rubber dam around a tooth at one end of a dental arch. The clamp includes a projecting arm extending toward the gingival tissue adjacent the distal of the tooth. The arm retracts the gingival tissue and rubber dam from the distal of the end tooth to allow instrument access thereto.

15 Claims, 5 Drawing Figures

DISTAL RETRACTION CLAMP FOR RUBBER DAM

BACKGROUND OF THE INVENTION

1. Field of the Invention

This invention relates to a rubber dam retaining clamp and, more particularly, to a clamp which retracts the gingival tissue and dam from the distal of the rearmost tooth of the dental arch.

2. Description of the Prior Art

In the practice of dentistry, a thin rubber sheet, known as a rubber dam, is commonly placed around one or more teeth, with the teeth perforating the dam to provide an exposed saliva-free tooth area on which to work. In order to retain the rubber dam around the teeth, retaining clamps having opposed, spring-biased jaws engaging opposite sides of a tooth are used to retain the dam against the gingival tissue. Typical such clamps are shown in U.S. Pat. Nos. 158,376; 1,496,541 and 1,970,875.

Gingival tissue distal to the rearmost tooth normally extends toward the distal marginal ridge or overlaps the ridge to form a flap-like projection partially covering the occlusal surface of the tooth. When it is necessary to restore this surface, the dentist is confronted with the problem of retracting the gingival tissue extending along the distal surface and holding back the rubber dam therefrom. Existing retaining clamps are not adequate to solve this problem.

SUMMARY OF THE INVENTION

It is an object of the invention to provide a rubber dam retaining clamp of simple and economical construction which effectively retracts the gingival tissue and rubber dam from the distal surface of the rearmost tooth in a dental arch and is easy to apply.

Another object of the invention is to provide a distal retraction clamp which allows clear vision and instrument access to the distal surface of the tooth.

It is still another object of the invention to provide a retaining foot which attaches to a conventional rubber dam retaining clamp to retract the gingival tissue and rubber dam from the distal surface of the rearmost tooth.

These and other objects of the invention are accomplished by a distal retraction clamp having an arm extending from the clamp which contacts the distal area of the tooth at the gum line. The arm adequately retracts both the gingival tissue and rubber dam to provide a sufficient operating area for restoring the distal surface of the tooth. In a first embodiment, a single retracting arm projects from from the center of the spring arch connecting the two opposed jaws of the clamp. In an alternative embodiment, a pair of retracting arms on opposite sides of the clamp extend horizontally toward each other along the distal of the tooth. In another embodiment, a retracting foot similar to the first embodiment is provided having a mounting bracket for attachment to the spring arch whereby a standard rubber dam retaining clamp may be converted into a distal retaining clamp.

DETAILED DESCRIPTION OF THE INVENTION

Figure 1:
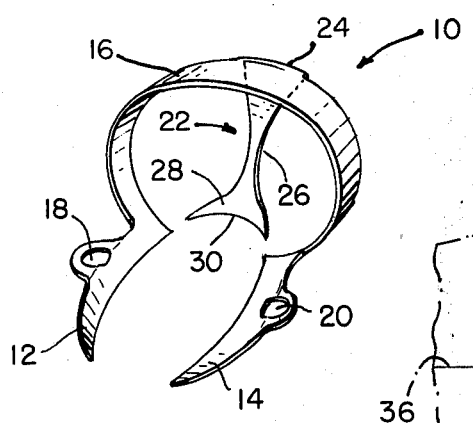
FIG. 1 is an isometric view of a first embodiment of the distal retraction clamp.
Figure 2:
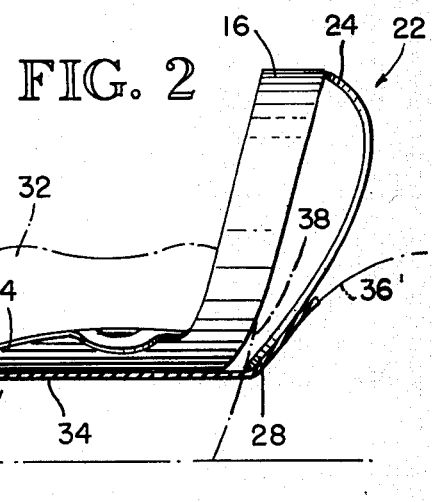
FIG. 2 is a side elevational view of the clamp of FIG. 1 installed on the last remaining tooth of a dental arch.
Figure 3:
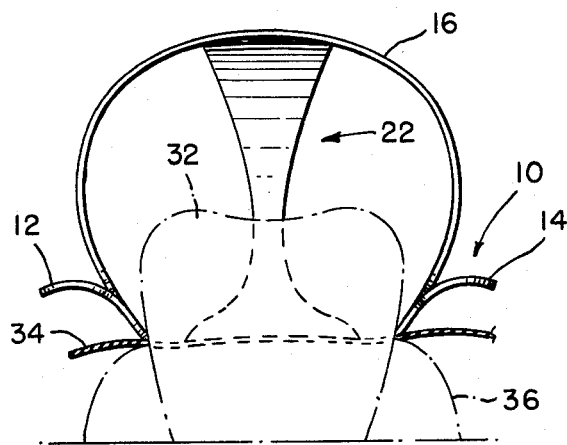
FIG. 3 is a front elevational view of the clamp of FIG. 1 installed on a tooth.

The distal retraction clamp 10 of the first embodiment of the present invention is illustrated in FIGS. 1-3 and includes conventional opposed jaws 12, 14 interconnected at the rear by a spring arch 16 which preferably slopes somewhat to the rear at an obtuse angle to the jaws as seen in FIG. 2. The jaws 12, 14 include respective holes 18, 20 which are adapted to receive a forceps for spreading the jaws 12, 14 apart to allow installation and removal of the clamp 10. The inside opposed edges of the jaws 12, 14 are curved concavely to generally conform to the convex side faces of the tooth.

In accordance with this invention, an integrally formed distal arm 22 cantilevers from the center of the arch 16 toward the plane of the jaws 12, 14. The distal arm 22 comprises a rearwardly arched spring metal piece having a root-end attachment portion 24 of increased width, a relatively bendable central portion 26 of decreased width, and a jaw-like retractor portion 28 having an increased width and a concave terminating edge 30.

In FIGS. 2 and 3, the clamp 10 is shown installed on the last remaining tooth 32 in a dental arch. The tooth 32 projects through a rubber dam 34 which completely surrounds the tooth and is retained in position by the jaws 12, 14 of the clamp 10 which contact the sides of the tooth 32 and press the dam against the gingival tissue 36. The distal arm 22 projects and arches rearwardly from the spring arch 16 to spring-urge the edge 30 of the retractor portion against the distal area 30 of the tooth 32, thereby retracting the rubber dam 34 and gingival tissue 36' behind the distal surface 38, as best illustrated in FIG. 2.

It will be noted that the rearward extension of the arching of the distal arm 22 is concentrated adjacent the spring arch 16 and that, since the central portion 26 is narrowed, the fore and aft bending motion necessary to properly position the edge 30 against the tooth primarily occurs in the central portion 26. This arrangement, together with the rearward slope of the arch 16, places the major portion of the arm 22 a sufficient distance behind the distal surface 38 to provide adequate instrument access thereto.

The distal arm 22 is shown here as formed together with the rest of the clamp from a sheet of spring metal. However, it will be understood that the arm may be a spring bar or wire secured to the arch 16 and having a retractor portion formed or added to its free end. Also, it is not necessary that the tooth-contacting edge 30 of the retractor portion be widened since, under certain circumstances, a narrow retractor portion may be desirable, particularly where the portion to be restored is near the retractor portion.

Figure 4:
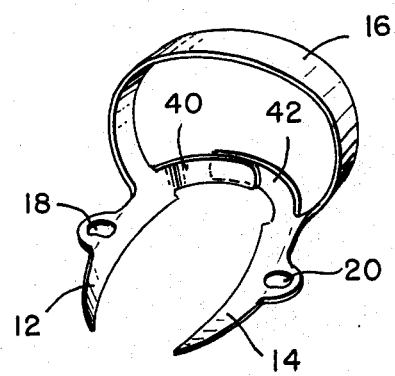
FIG. 4 is an isometric view of a second embodiment of the distal retraction clamp.

An alternative embodiment of a distal retraction clamp is illustrated in FIG. 4. Like the clamp of the first embodiment, the clamp includes opposed jaws 12, 14 containing respective forceps access holes 18, 20 and interconnected through a spring arch 16. In place of the arm 22, the clamp of the second embodiment includes a pair of elongated retracting arms 40, 42 extending toward each other in overlapping relation from the lower rear edge of the spring arch 16. These retracting arms collectively arch rearwardly and have a spring action so that the front concave surfaces of the arms will contact the distal surface of the tooth to retract the gingival tissue and rubber dam behind the tooth. Since the width of the arms 40, 42 is substantially less than the height from the gum line to the crown of the tooth, the major portion of the distal surface of the tooth is accessible to allow restoration thereof. Since the arms 40, 42 overlap each other, retraction along the entire width of the distal surface is assured, even when the clamp is used with teeth having differing widths.

Figure 5:
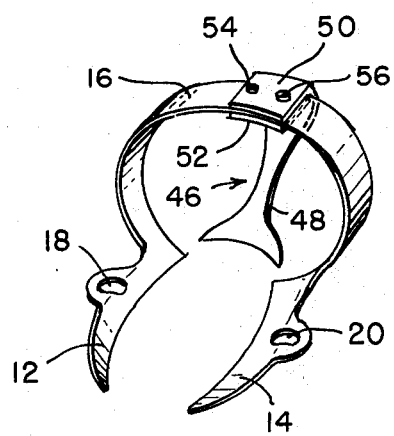
FIG. 5 is an isometric view of a third embodiment providing a retracting foot attached to a conventional retaining clamp for converting the clamp into a distal retraction clamp.

A retraction foot 46 which may be attached to a conventional rubber dam retaining clamp for converting the clamp into a distal retraction clamp is shown in FIG. 5. The foot 46 includes a distal arm 48 of identical construction to the arm 22 of the first embodiment except that it has a mount 50, 52 which clamps to the midsection of the spring arch 16 rather than being formed integrally therewith. The mount comprises a substantially rigid pad having a center slot open at the front between opposed clamping plates for receiving the spring arch 16. A pair of set screws 54, 56 engage threaded through-bores in the top mounting plate 50 and are torqued against the top of the spring arch 16 to fix the position of the retracting foot with respect to the clamp.

The embodiments of the invention in which a particular property or privilege is claimed are defined as follows:

1. In a rubber dam retaining clamp of the type including a spring arch connecting a pair of opposed jaws for gripping respective inner and outer sides of a tooth in a dental arch adjacent the gum line, the improvement comprising arm means connected to said clamp and adapted to contact the distal area of the rearmost tooth in the arch adjacent the gum line for retracting the distal gingival tissue and overlying portion of a rubber dam through which the tooth projects.

2. The distal retraction clamp of claim 1 wherein said arm means comprises an elongated member of spring metal extending at one end from the center portion of said spring arch in the general direction of said jaws and with the other end of said elongated member being formed to contact the distal area of said tooth to retract the distal gingival tissue and rubber dam therefrom.

3. The distal retraction clamp of claim 2 wherein said other end of the elongated member includes a retractor portion having a concave edge for abutting the distal surface of said tooth.

4. The distal retraction clamp of claim 3 wherein said retractor portion is of increased width with respect to the remainder of said elongated member.

5. The distal retraction clamp of claim 3 wherein said elongated member is a sheet of material having a relatively bendable portion of reduced width intermediate said spring arch and retractor portion.

6. The distal retraction clamp of claim 2 in which said elongated member has spring characteristics and arches said elongated member has spring characteristics and arches rearwardly with the rearward extension of such member being concentrated near said spring arch.

7. The distal retraction clamp of claim 1 in which said spring arch slopes rearwardly from said jaws to its connection with said arm means.

8. The distal retraction clamp of claim 7 in which said arm means arches rearwardly relative to said spring arch.

9. The distal retraction clamp of claim 1 in which said jaws, spring arch and arm means are integral with one another.

10. The distal retraction clamp of claim 1 wherein said arm means comprise a pair of elongated retracting arms connected to respective ends of said spring arch adjacent said jaws, said retracting arms extending toward each other with the forward surfaces of said arms adapted to contact the distal area of said tooth to retract the gingival tissue and rubber dam therefrom.

11. The distal retraction clamp of claim 10 wherein said retaining arms overlap and arch rearwardly to generally conform to the distal surface of said tooth whereby the forward concave surfaces of said arms contact said tooth along a substantial part of the length of said arms.

12. The distal retraction clamp of claim 10 wherein the width of said retracting arms is substantially less than the height of a tooth so that the major portion of said distal area will be accessible adjacent said retracting arms.

13. The distal retraction clamp of claim 1 in which said arm means has mounting means for detachably connecting the arm means to said spring arch.

14. A retraction foot adapted to be attached to a rubber dam retaining clamp of the type having a pair of opposed jaws connected to opposite ends of a spring arch for retracting gingival tissue and a rubber dam from a tooth to which the clamp is secured, said retraction foot comprising:
a detachable mount having a slot for receiving said spring arch and including means associated with said mount for engaging the arch to retain the arch in the slot; and
an elongated member of spring metal secured to said mount, said elongated member having a retractor portion adapted to abut the distal surface of the rearmost tooth and retract the distal gingival tissue and rubber dam when said clamp is applied to such tooth.

15. The retraction foot of claim 14 wherein said means for engaging said spring arch comprise a pair of set screws extending through threaded bores in said mount to frictionally contact said spring arch.

* * * * *